(12) United States Patent
Xu et al.

(10) Patent No.: US 10,307,510 B2
(45) Date of Patent: *Jun. 4, 2019

(54) METHODS OF REMOVING ALPHA-GALACTOSE

(71) Applicant: LifeCell Corporation, Branchburg, NJ (US)

(72) Inventors: Hui Xu, Plainsboro, NJ (US); Li Ting Huang, Branchburg, NJ (US); Hua Wan, Princeton, NJ (US); Rick T. Owens, Stewartsville, NJ (US); Nathaniel Bachrach, Clifton, NJ (US)

(73) Assignee: LifeCell Corporation, Madison, NJ (US)

( * ) Notice: Subject to any disclaimer, the term of this patent is extended or adjusted under 35 U.S.C. 154(b) by 261 days.

This patent is subject to a terminal disclaimer.

(21) Appl. No.: 14/532,089

(22) Filed: Nov. 4, 2014

(65) Prior Publication Data

US 2015/0126453 A1     May 7, 2015

Related U.S. Application Data

(60) Provisional application No. 61/899,647, filed on Nov. 4, 2013.

(51) Int. Cl.
| | |
|---|---|
| *A61L 27/36* | (2006.01) |
| *A61L 27/24* | (2006.01) |
| *A61L 27/54* | (2006.01) |
| *A61L 27/58* | (2006.01) |
| *G01N 33/573* | (2006.01) |

(52) U.S. Cl.
CPC ........... *A61L 27/3687* (2013.01); *A61L 27/24* (2013.01); *A61L 27/3695* (2013.01); *A61L 27/54* (2013.01); *A61L 27/58* (2013.01); *G01N 33/573* (2013.01); *A61L 2300/412* (2013.01); *A61L 2430/34* (2013.01); *A61L 2430/40* (2013.01)

(58) Field of Classification Search
CPC ............................ A61L 27/3687; A61L 27/24
See application file for complete search history.

(56) References Cited

U.S. PATENT DOCUMENTS

| | | |
|---|---|---|
| 4,098,571 A | 7/1978 | Miyata et al. |
| 4,801,299 A | 1/1989 | Brendel et al. |
| 5,116,615 A | 5/1992 | Gokcen et al. |
| 5,336,616 A | 8/1994 | Livesey et al. |
| 5,364,756 A | 11/1994 | Livesey et al. |
| 5,374,539 A | 12/1994 | Nimni et al. |
| 5,460,962 A | 10/1995 | Kemp |
| 5,547,681 A | 8/1996 | Clark et al. |
| 5,782,915 A | 7/1998 | Stone |
| 5,821,117 A | 10/1998 | Sandrin et al. |
| 5,846,715 A | 12/1998 | Purcell et al. |
| 5,849,991 A | 12/1998 | d'Apice et al. |
| 5,855,620 A | 1/1999 | Bishopric et al. |
| 6,096,347 A | 8/2000 | Geddes et al. |
| 6,099,567 A | 8/2000 | Badylak et al. |
| 6,130,062 A | 10/2000 | Milland et al. |
| 6,153,428 A | 11/2000 | Gustafsson et al. |
| 6,166,288 A | 12/2000 | Diamond et al. |
| 6,267,786 B1 * | 7/2001 | Stone ................... A61L 27/3604 623/13.17 |
| 6,331,658 B1 | 12/2001 | Cooper et al. |
| 6,371,992 B1 | 4/2002 | Tanagho et al. |
| 6,379,710 B1 | 4/2002 | Badylak |
| 6,381,026 B1 | 4/2002 | Schiff et al. |
| 6,413,769 B1 | 7/2002 | Gustafsson et al. |
| 6,423,316 B1 | 7/2002 | Riesbeck et al. |
| 6,432,710 B1 | 8/2002 | Boss, Jr. et al. |
| 6,455,037 B1 | 9/2002 | Ioannou et al. |
| 6,455,309 B2 | 9/2002 | Stone |
| 6,482,404 B1 | 11/2002 | White et al. |
| 6,495,735 B1 | 12/2002 | White et al. |
| 6,613,278 B1 | 9/2003 | Mills et al. |
| 6,652,818 B1 | 11/2003 | Mills et al. |
| 6,734,018 B2 | 5/2004 | Wolfinbarger, Jr. et al. |
| 6,743,574 B1 | 6/2004 | Wolfinbarger, Jr. et al. |
| 6,783,776 B2 | 8/2004 | Spievack |
| 6,835,385 B2 | 12/2004 | Buck |
| 6,849,448 B1 | 2/2005 | D'Apice et al. |
| 6,933,103 B1 | 8/2005 | Klein et al. |
| 6,933,326 B1 | 8/2005 | Griffey et al. |
| 6,936,271 B1 | 8/2005 | Oliver et al. |
| 7,001,998 B2 | 2/2006 | McKenzie et al. |
| 7,067,298 B2 | 6/2006 | Latham et al. |
| 7,118,901 B2 | 10/2006 | Suppmann et al. |
| 7,126,039 B2 | 10/2006 | Denning et al. |
| 7,201,899 B2 | 4/2007 | d'Apice et al. |
| 7,318,998 B2 | 1/2008 | Goldstein et al. |
| 7,354,749 B2 | 4/2008 | Fisher et al. |
| 7,358,284 B2 | 4/2008 | Griffey et al. |
| 7,368,284 B2 | 5/2008 | Koike |
| 7,402,319 B2 | 7/2008 | Schmidt et al. |
| 7,432,344 B1 | 10/2008 | Lechler et al. |
| 7,498,412 B2 | 3/2009 | Huang et al. |
| 7,595,377 B2 | 9/2009 | Stone |
| 7,628,996 B2 | 12/2009 | Haspel et al. |

(Continued)

FOREIGN PATENT DOCUMENTS

| | | |
|---|---|---|
| CA | 2286655 A1 | 10/1998 |
| CA | 2396698 A1 | 8/2001 |

(Continued)

OTHER PUBLICATIONS

Galili, The alpha-gal epitope and the anti-Gal antibody in xenotransplantation and in cancer immunotherapy, Immunology and Cell Biology, vol. 83, p. 674-686. (Year: 2005).*

(Continued)

*Primary Examiner* — Taeyoon Kim
*Assistant Examiner* — Tiffany M Gough
(74) *Attorney, Agent, or Firm* — McCarter & English, LLP

(57) ABSTRACT

Tissue products lacking a desired percentage of immunogenic epitopes, such as galactose alpha-1,3 galactose epitopes, are provided. Methods of making and using the tissue products are also provided.

18 Claims, 2 Drawing Sheets

(56) References Cited

U.S. PATENT DOCUMENTS

| | | | |
|---|---|---|---|
| 7,723,108 B2 | 5/2010 | Truncale et al. |
| 7,763,081 B2 | 7/2010 | Ollerenshaw et al. |
| 8,236,335 B2 | 8/2012 | Baker, Jr. et al. |
| 8,324,449 B2 | 12/2012 | McQuillan et al. |
| 9,206,442 B2 | 12/2015 | Chen |
| 9,238,793 B2 | 1/2016 | Chen et al. |
| 9,259,511 B2 | 2/2016 | Sun |
| 9,956,316 B2 | 5/2018 | Chen |
| 9,957,477 B2 | 5/2018 | Chen et al. |
| 10,022,473 B2 | 7/2018 | Sun |
| 2002/0077697 A1 | 6/2002 | Ranieri et al. |
| 2002/0114845 A1 | 8/2002 | DeVore et al. |
| 2002/0115208 A1 | 8/2002 | Mitchell et al. |
| 2003/0014126 A1 | 1/2003 | Patel et al. |
| 2003/0014770 A1 | 1/2003 | Gustafsson et al. |
| 2003/0035843 A1 | 2/2003 | Livesey et al. |
| 2003/0068815 A1 | 4/2003 | Stone et al. |
| 2003/0068818 A1 | 4/2003 | Denning et al. |
| 2003/0092174 A1 | 5/2003 | Liljedahl et al. |
| 2003/0131365 A1 | 7/2003 | Cooper et al. |
| 2003/0143207 A1 | 7/2003 | Livesey et al. |
| 2003/0159161 A1 | 8/2003 | Graham et al. |
| 2003/0165480 A1 | 9/2003 | Zhu |
| 2003/0203427 A1 | 10/2003 | Koike |
| 2004/0006395 A1 | 1/2004 | Badylak |
| 2004/0064842 A1 | 4/2004 | Graham et al. |
| 2004/0067582 A1 | 4/2004 | Wolfinbarger et al. |
| 2004/0076657 A1 | 4/2004 | Wolfinbarger et al. |
| 2004/0115172 A1 | 6/2004 | Bianchi et al. |
| 2004/0115616 A1 | 6/2004 | Holton |
| 2004/0171155 A1 | 9/2004 | d'Apice et al. |
| 2004/0175366 A1 | 9/2004 | Badylak |
| 2004/0176855 A1 | 9/2004 | Badylak |
| 2004/0180439 A1 | 9/2004 | Graham et al. |
| 2004/0187877 A1* | 9/2004 | Badylak ............... A61K 35/407 128/898 |
| 2004/0191226 A1 | 9/2004 | Badylak |
| 2004/0234507 A1 | 11/2004 | Stone |
| 2004/0243250 A1 | 12/2004 | Stone et al. |
| 2004/0249317 A1 | 12/2004 | Hung et al. |
| 2004/0268424 A1 | 12/2004 | Phelps |
| 2005/0013870 A1 | 1/2005 | Freyman et al. |
| 2005/0028228 A1 | 2/2005 | McQuillan et al. |
| 2005/0076399 A1 | 4/2005 | Lee et al. |
| 2005/0096742 A1 | 5/2005 | Mills et al. |
| 2005/0118160 A1 | 6/2005 | Riesbeck et al. |
| 2005/0120400 A1 | 6/2005 | Day et al. |
| 2005/0155095 A1 | 7/2005 | Koike |
| 2005/0186286 A1 | 8/2005 | Takami |
| 2005/0191281 A1 | 9/2005 | Ollerenshaw et al. |
| 2005/0256588 A1 | 11/2005 | Sawa et al. |
| 2005/0260176 A1 | 11/2005 | Ayares et al. |
| 2005/0266561 A1 | 12/2005 | Wells |
| 2006/0068479 A1 | 3/2006 | Koike |
| 2006/0073592 A1 | 4/2006 | Sun et al. |
| 2006/0127375 A1 | 6/2006 | Livesey et al. |
| 2006/0210960 A1 | 9/2006 | Livesey et al. |
| 2006/0242722 A1 | 10/2006 | Hawley |
| 2006/0272102 A1 | 12/2006 | Liu et al. |
| 2006/0294610 A1 | 12/2006 | Koike |
| 2007/0009586 A1 | 1/2007 | Cohen et al. |
| 2007/0010897 A1 | 1/2007 | Stone |
| 2007/0089178 A1 | 4/2007 | Zhu |
| 2007/0123700 A1 | 5/2007 | Ueda et al. |
| 2007/0248575 A1 | 10/2007 | Connor et al. |
| 2008/0027562 A1 | 1/2008 | Fujisato et al. |
| 2008/0181935 A1 | 7/2008 | Bhatia et al. |
| 2008/0188939 A1 | 8/2008 | DePaula et al. |
| 2008/0250517 A1 | 10/2008 | Colman et al. |
| 2008/0306610 A1 | 12/2008 | Wang et al. |
| 2009/0049562 A1 | 2/2009 | Koike |
| 2009/0130221 A1 | 5/2009 | Bolland et al. |
| 2009/0186333 A1 | 7/2009 | Mills et al. |
| 2009/0202977 A1 | 8/2009 | Ott et al. |
| 2009/0239809 A1 | 9/2009 | Chen et al. |
| 2009/0306790 A1 | 12/2009 | Sun |
| 2010/0112543 A1 | 5/2010 | Ngo et al. |
| 2010/0119577 A1 | 5/2010 | Min et al. |
| 2010/0179639 A1 | 7/2010 | Bloor et al. |
| 2010/0196870 A1 | 8/2010 | Stone et al. |
| 2010/0233235 A1 | 9/2010 | Matheny et al. |
| 2010/0291172 A1 | 11/2010 | Drunecky |
| 2011/0021753 A1 | 1/2011 | Huang |
| 2011/0064782 A1 | 3/2011 | Bloor et al. |
| 2012/0252065 A1 | 10/2012 | Rozenszain et al. |
| 2012/0276213 A1 | 11/2012 | Chen |
| 2013/0013068 A1 | 1/2013 | Forsell et al. |
| 2013/0028981 A1 | 1/2013 | Gratzer |
| 2013/0236439 A1 | 9/2013 | Sun et al. |
| 2014/0377833 A1 | 12/2014 | Chen et al. |
| 2016/0045639 A1 | 2/2016 | Chen |
| 2016/0090572 A1 | 3/2016 | Chen et al. |
| 2016/0114080 A1 | 4/2016 | Sun |
| 2018/0216062 A1 | 8/2018 | Chen et al. |

FOREIGN PATENT DOCUMENTS

| | | |
|---|---|---|
| CN | 1266716 A | 9/2000 |
| EP | 0770137 A1 | 5/1997 |
| EP | 1000161 A1 | 5/2000 |
| EP | 1073737 A2 | 2/2001 |
| EP | 1141265 A1 | 10/2001 |
| GB | 2443938 A | 5/2008 |
| GB | 2482166 A | 1/2012 |
| JP | 2004-107303 A | 4/2004 |
| WO | WO-95/20661 A1 | 8/1995 |
| WO | WO-95/28412 A1 | 10/1995 |
| WO | WO-95/34202 A1 | 12/1995 |
| WO | WO-1996/032905 A1 | 10/1996 |
| WO | 1999/00152 A2 | 1/1999 |
| WO | WO-1999/044533 A1 | 9/1999 |
| WO | WO-99/65470 A1 | 12/1999 |
| WO | WO-2000/047131 A1 | 12/2000 |
| WO | WO-01/88096 A2 | 11/2001 |
| WO | WO-01/91671 A1 | 12/2001 |
| WO | WO-02/14480 A2 | 2/2002 |
| WO | WO-02/074948 A2 | 9/2002 |
| WO | WO-02/088351 A1 | 11/2002 |
| WO | WO-03/097694 A1 | 11/2003 |
| WO | WO-2004/020470 A1 | 3/2004 |
| WO | WO-2005/009497 A1 | 2/2005 |
| WO | WO-2005/089411 A2 | 9/2005 |
| WO | WO-2006/095342 A2 | 9/2006 |
| WO | WO-2006/101885 A2 | 9/2006 |
| WO | WO-07/43513 A1 | 4/2007 |
| WO | WO-08/125850 A2 | 10/2008 |
| WO | WO-2008154623 A2 | 12/2008 |
| WO | WO-2008154628 A2 | 12/2008 |
| WO | 2009/049568 A2 | 4/2009 |
| WO | 2009/133532 A1 | 11/2009 |
| WO | 2013/067598 A1 | 5/2013 |

OTHER PUBLICATIONS

Badylak et al., "Extracellular Matrix as a Biological Scaffold Material: Structure and Function," Acta Biomaterialia (2008), doi:10.1016/j.actbio.2008.09.013.

Collins et al., "Cardiac Xenografts Between Primate Species Provide Evidence for the Importance of the .alpha.-Galactosyl Determinant in Hyperacute Rejection," J. Immunol. 154:5500-5510 (1995).

Galili et al., "Interaction between human natural anti-alpha-galactosyl immunoglobulin G and bacteria of the human flora," Infect. Immun. 56:1730-1737 (1988).

Galili et al., "Interaction of the natural anti-Gal antibody with .alpha.-galactosyl epitopes: a major obstacle for xenotransplantation in humans," Immunology Today 14: 480-482 (1993).

Galili et al., "Man, apes, and Old World monkeys differ from other mammals in the expression of alpha-galactosyl epitopes on nucleated cells," J. Biol. Chem. 263:17755-17762 (1988).

(56) References Cited

OTHER PUBLICATIONS

Good et al., "Identification of Carbohydrate Structures That Bind Human Antiporcine Antibodies: Implications for Discordant Xenografting in Humans," Transplant Proc. 24: 559-562 (1992).
Hamadeh et al., "Human natural anti-Gal IgG regulates alternative complement pathway activation on bacterial surfaces," J. Clin. Invest. 89:1223-1235 (1992).
Ionescu et al., "Effect of Papain and Bromelin on Muscle and Collagen Proteins in Beef Meat," The Annals of the University Dunarea de Jos of Galati. Fascicle VI, Food Technology, New Series, pp. 9-16, 2008.
Sandrin et al., "Anti-pig IgM antibodies in human serum react predominantly with Gal(alpha 1-3)Gal epitopes," Proc. Natl. Acad. Sci. USA 90: 11391-11395 (1993).
Xu, "A Porcine-Derived Acellular Dermal Scaffold that Supports Soft Tissue Regeneration: Removal of Terminal Galactose-.alpha.-(1,3)-Galactose and Retention of Matrix Structure," Tissue Engineering, vol. 15, 1-13 (2009).
Dobrin, P.B. et al. "Elastase, collagenase, and the biaxial elastic properties of dog carotid artery" Am. J. Physiol. Heart Circ. Physiol. 247:H124-H131 (1984).
Karlinsky, J.B. et al. "In Vitro Effects of Elastase and Collagenase on Mechanical Properties of Hamster Lungs" Chest 69(2):275-276 (1976).
Lu, Q. et al. "Novel Porous Aortic Elastin and Collagen Scaffolds for Tissue Engineering" Biomaterials 25(22):5227-5237 (2004).
Reihsner, R. et al. "Biomechanical properties of elastase treated palmar aponeuroses" Connective Tissue Research 26:77-86 (1991).
Tedder, M.E. et al. "Stabilized Collagen Scaffolds for Heart Valve Tissue Engineering" Tissue Engineering: Part A 00(00):1-12 (2008).
Yuan, H. et al. "Effects of collagenase and elastase on the mechanical properties of lung tissue strips" J. App. Physiol. 89:3-14 (2000).
Parenteau-Bareil et al. "Collagen-Based Biomaterials for Tissue Engineering Applications," Materials, 3:1863-1887 (2010).
Gilbert et al. "Decellulaization of tissues and organs," Biomaterials, 27:3675-3683 (2006).
Chaplin, J.M. et al. "Use of an Acellular Dermal Allograft for Dural Replacement: An Experimental Study" Neurosurgery 45(2):320-327 (1999).
Denning et al., "New Frontiers in Gene Targeting and Cloning: Success, Application and Challenges in Domestic Animals and Human Embryonic Stem Cells," Reproduct. 126:1-11 (2003).
Krejci, N. C. et al. "In Vitro Reconstitution of Skin: Fibroblasts Facilitate Keratinocyte Growth and Differentiation on Acellular Reticular Dermis" J Invest Dermatol 97:843-848 (1991).
Sandrin, M.S. et al. "Enzymatic remodelling of the carbohydrate surface of a xenogenic cell substantially reduces human antibody binding and complement-mediated cytolysis" Nature Medicine 1(12):1261-1267 (1995).
Sharma, A. et al. "Reduction in the level of Gal(.alpha.1,3)Gal in transgenic mice and pigs by the expression of an .alpha.(1,2)fucosyltransferase" Proc. Natl. Acad. Sci. USA 93:7190-7195 (1996).
Taylor, S.G. et al. "Reduction of .alpha.-Gal expression by relocalizing .alpha.-galactosidase to the trans-Golgi network and cell surface" Glycobiology 12(11):729-739 (2002).
Thall, A.D. et al. "Oocyte Gal.alpha.1,3Gal Epitopes Implicated in Sperm Adhesion to the Zona Pellucida Glycoprotein ZP3 Are Not Required for Fertilization in the Mouse" J. Biol. Chem. 270(37):21437-21440 (1995).
Zheng, M.H. et al. "Porcine Small Intestine Submucosa (SIS) Is Not an Acellular Collagenous Matrix and Contains Porcine DNA: Possible Implications in Human Implantation" J. Biomed. Mater. Res. Part B: Appl. Biomater. 73B:61-67 (2005).
Simon et al., "Early failure of the tissue engineered porcine heart valve Synergrafttm in pediatric patients," European Journal of Cardio-thoracic Surgery 23 (2003) 1002-1006.
Gratzer et al., "Altered mechinal properties in aortic elastic tissue using glutaraldehyde/solvent solutions of various dielectric constant," J Biomed Mater Res, 37, 497-507 (1997).
Gratzer et al., "Solvent environment modulates effects of glutaraldehyde crosslinking on tissue-derived biomaterials," J. Biomed. Mater. Res., 31, 533-543 (1996).
Gopinath et al., "Effect of aqueous ethanol on the triple helical structure of collagen," Eur Biophys J., 43, 643-652 (2014).
Woods et al., "Effectiveness of three extraction techniques in the development decellularized bone-anterior cruciate ligament-bone graft," Biomaterials, 26, 7339-7349 (2005).
Gratzer et al., "Matrix Alteration and Not Residual Sodium Dodecyl Sulfate Cytotoxicty Affects the Cellular Repopulation of a Decellularized Matrix," Tissue Engineering, 12(10), 2975-2984 (2006).
Kitagawa et al., "Cellular biology of cryopreserved allograft valves," The Journal of Medcial Investigation, 48, 123-132 (2001).
Kearney et al., "Guidelines on processing and clinical use of skin allografts," Clinics in Dermatology, 23, 357-364 (2005).
Azar, "Tissue Processing: Role of Secondary Sterilization Techniques," Clin Sports Med, 28, 191-201 (2009).
Wainwright, "Use of an acellular allograft dermal matrix (AlloDerm) in the management of full-thickness burns," Burns, 21(4), 243-248 (1995).
Eberli et al., "In vivo evaluation of acellular human dermis for abdominal wall repair," J. Biomed Mater Res 93A:1527-1538 (2010).
Faleris et al., "In-vivo and in-vitro histological evaluation of two commercially available acellular dermal matrices," Hernia, 15, 147-156 (2011).
Scheffler et al., Remodeling of ACL Allografts is Inhibited by Peracetic Acid Sterilization, Clin Orthop Relat Res, 466, 1810-1818 (2008).
Hodde et al., "Effects of sterilization on an extracellular matrix scaffold: Part I. Composition and matrix architecture," J Mater Sci. Mater Med, 15, 537-543 (2007).
Bonenfant et al., "The effects of storage and sterilization on decellularized and re-cellularized whole lung," Biomaterials, 34, 3231-3245 (2013).
Whitlock et al., "A naturally derived, cytocompatible, and architecturally optimized scaffold for tendon and ligament regeneration," Biomaterials, 28, 4321-4329 (2007).
Horowitz et al.,"Viral safety of solvent-detergent treated blood products," Dev. Biol. Stand., vol. 81, pp. 147-161, 1993.
Leyh et al., "Acellularized porcine heart valve scaffolds for heart valve tissus engineering and the risk of cross-species transmission of porcine endogenous retrovirus," J. Thorac. Cardiovasc. Surg., vol. 126, No. 4, pp. 1000-1004, Oct. 2003.
Walles et al., "In vivo model for cross-species porcine endogenous retrovirus transmission using tissue engineered pulmonary arteries," European Journal of Cardio-thoracic Surgery, vol. 24, No. 3, pp. 358-363, Sep. 2003.
Williams et al., "Altered structural and mechanical properties in decellularized rabbit carotid arteries," Acta Biomater., vol. 5, No. 4, pp. 993-1005, May 2009.
Wilson et al., "Acellular Matrix: A Biomaterial Approach for Coronary Artery Bypass and Heart Valve Replacement," Ann. Thorac. Surg. vol. 60, Suppl. 2, pp. S353-S358, Aug. 1995.
International Preliminary Report on Patentability for International Application No. PCT/US2014/063796, dated May 10, 2016.
Grauss et al. "Histological Evaluation of Decellularised Porcine Aortic Valves: Matrix Changes Due to Different Decellularisation Methods," European Journal of Cardio-Thoracic Surgery, 27(4): 566-571, 2005.
Courtman et al. "Development of a Pericardial Acellular Matrix Biomaterial: Biochemical and Mechanical Effects of Cell Extraction", Journal of Biomedical Materials Research, XP000878572, 28(6): 655-666, Jan. 1, 1994.
Kim et al. "Time Related Histopathologic Changes Acellularized Xenogenic Pulmonary Valved Conduits", ASAIO Journal, 50(6): 601-605, 2004.
Zeltinger et al. "Development and Characterization of Tissue-Engineered Aortic Valves", Tissue Engineering, 7(1): 9-22, 2001. Abstract, P.10, Paragraph 5-P.11, Paragraph 1, Fig.6.
Galili et al., Interaction between human natural anti-alpha-galactosyl immunoglobulin G and bacteria of the human flora. Infect Immun. Jul. 1988;56(7):1730-7.

(56) References Cited

OTHER PUBLICATIONS

Oliver et al., Histological Studies of Subcutaneous and Intraperitoneal Implants of Trypsin-Prepared Dermal Collagen Allografts in the Rat. Clinical Orthopaedics and Related Research. Mar.-Apr. 1976;115;291-302.

Wang et al., Comparison between Thermal Hydrolysis and Enzymatic Proteolysis Processes for the Preparation of Tilapia Skin Collagen Hydrolysates. Czech J Food Sci. 2013;31(1):1-4.

* cited by examiner

METHODS OF REMOVING ALPHA-GALACTOSE

The present disclosure relates generally to methods of preparing and using tissue matrices lacking some or all galactose alpha-1,3-galactose epitopes.

Various tissue-derived products are used to repair, regenerate, heal, or otherwise treat diseased or damaged tissues and organs. Such products can include intact tissue grafts and/or partially or completely decellularized tissues. These tissue products can be provided from various donor sources, including tissue harvested from the recipient (i.e., autografts), from another member of the same species (i.e., allografts), or from a different species (i.e., xenografts). While autografts and allografts may reduce the possibility of rejection due to the expression of species-specific proteins in the donor tissue, those donor sources may be impractical or incapable of providing sufficient material at the time of surgical use.

Accordingly, alternative xenograft sources may be sought. One issue with xenotransplantation is that the donor may express enzymes or other proteins in the tissue that are not expressed by the recipient, heightening the possibility of rejection. For instance, animals (e.g., humans or other primates) that do not express the enzyme UDP-galactose:beta-D-galactosyl-1,4-N-acetyl-D-glucosaminide alpha-1,3-galactosyltransferase ("alpha-1,3 galactosyltransferase" or "alpha GT"), which catalyzes the formation of the terminal disaccharide galactose alpha-1,3 galactose ("alpha-gal"), can exhibit an increased immune response and hyperacute rejection of xenografts from animals (e.g., pigs or other non-primate mammals) expressing the alpha-gal epitope on the surface of cells in a tissue graft.

Elimination of the alpha-gal epitopes from a tissue product may diminish the immune response against the composition. U. Galili et al., *J. Biol. Chem.* 263: 17755 (1988). As such, methods are needed for removing alpha-gal epitopes from donor tissues intended for implantation into recipients (e.g., humans) that do not express alpha-gal epitopes.

Accordingly, in various embodiments, methods are disclosed for removing alpha-gal from a decellularized tissue. The methods can comprise selecting at least one collagen-containing tissue matrix containing galactose alpha-1,3-galactose moieties; and contacting the at least one tissue matrix with at least one proteolytic enzyme under conditions sufficient to remove galactose alpha-1,3-galactose moieties from the tissue.

The enzymes can include alcalase, bromelain, dispase, or trypsin. And the method can further comprise performing an assay to determine if galactose alpha-1,3-galactose moieties have been removed from the at least collagen-containing tissue matrix.

Tissue products produced using the methods are also provided. In addition, methods of treatment using the tissue products or tissue products produced by the disclosed methods are provided. An enzymatically treated tissue product is further provided. The tissue product can include an acellular tissue matrix prepared from a wild-type porcine collagen-containing tissue, wherein the collagen-containing tissue has been enzymatically treated to remove substantially all galactose alpha-1,3-galactose moieties from the tissue using a protease that is not specifically directed towards galactose alpha-1,3-galactose moieties. In some embodiments, the tissue matrix is from a non-primate animal that produces alpha-galactose, and the tissue matrix has been further processes to substantially or completely remove alpha-galactose from the collagen-containing tissue matrix.

The at least one collagen-containing tissue matrix can be contained within a cellular tissue, and the method can further comprise decellularizing the cellular tissue. In some embodiments, the tissue matrix is completely decellularized; and the tissue matrix can comprise an acellular matrix.

In some embodiments, the proteolytic enzyme removes galactose alpha-1,3-galactose moieties without damaging the at least one tissue matrix.

In some embodiments, the assay comprises measuring a concentration of galactose alpha-1,3-galactose moieties. The assay can comprise an histochemical assay or an immuno assay.

The protease can include at least one of alcalase and trypsin, and the protease is used at a concentration ranging from about 0.0001% to about 0.1% and for a period of time ranging from about 0.5 hours to about 24 hours. The protease can also include at least one of bromelain and dispase, and the protease is used at a concentration ranging from about 10 units/liter to about 200 units/liter and for a period of time ranging from about 1 hour to about 24 hours. The method can further comprise contacting the tissue with an alpha-galactosidase.

The at least one collagen-containing tissue matrix can comprise a tissue matrix from at least one of bone, skin, adipose tissue, dermis, intestine, urinary bladder, tendon, ligament, muscle, fascia, vascular, neurologic, vessel, liver, heart, lung, kidney, and cartilage tissue. The tissue can be obtained from one or more different animals or tissue sources. The at least one collagen-containing tissue matrix can be a porcine tissue matrix such as a porcine acellular dermal tissue matrix The method can further comprise adding one or more viable and histocompatible cells to the tissue product, such as mammalian cells, including mammalian stem cells.

In some embodiments, at least one additional factor selected from an anti-inflammatory agent, an analgesic, a cell growth factor, an angiogenic factor, a differentiation factor, a cytokine, a hormone, and a chemokine is added to the tissue product. The at least one additional factor can be encoded by a nucleic acid sequence contained within an expression vector, which may be contained within one or more viable and histocompatible cells.

The method can further comprise treating the at least one collagen-containing tissue matrix to reduce bioburden. Treating the at least one collagen-containing tissue matrix to reduce bioburden can comprise irradiating the tissue product.

DESCRIPTION OF CERTAIN EXEMPLARY EMBODIMENTS

Figure 1A:
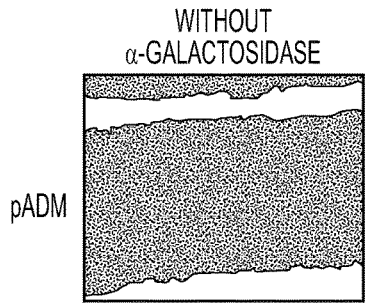
FIGS. 1A-1H are black and white drawings illustrating results of immunohistochemical staining for alpha-gal moieties with untreated porcine acellular dermis (no enzyme used to remove alpha-gal), and porcine acellular dermis samples treated with bromelain, alcalase, and trypisin, each with and without alpha-galactosidase treatment, according to the methods of Example 1.
Figure 1B:
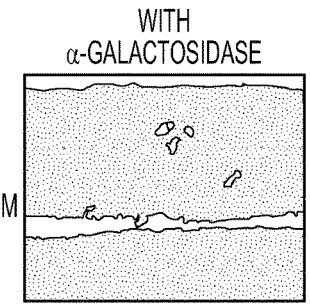
Figure 1C:
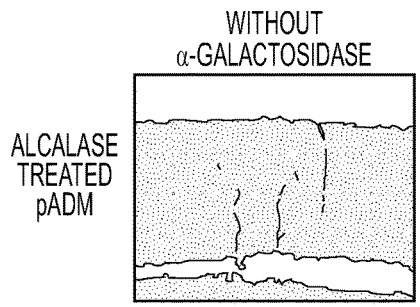
Figure 1D:
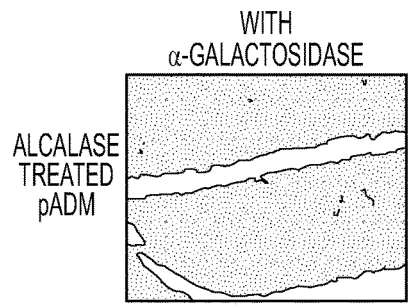
Figure 1E:
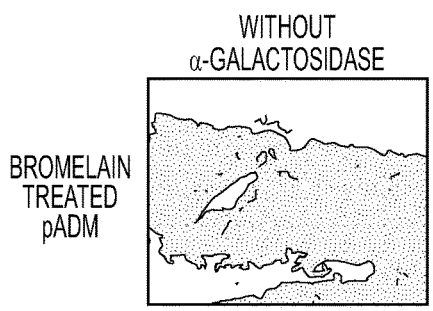
Figure 1F:
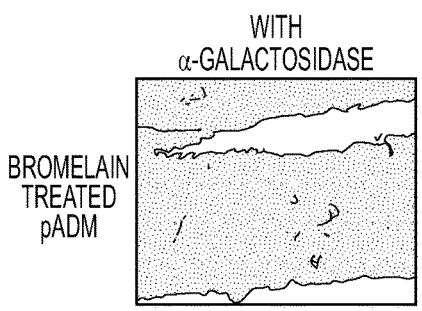
Figure 1G:
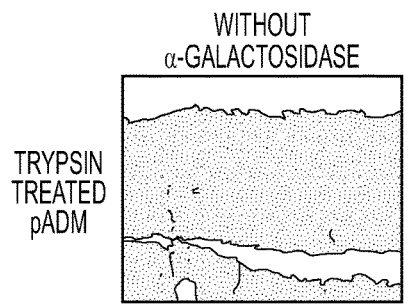
Figure 1H:
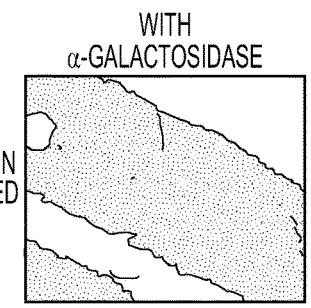

Reference will now be made in detail to certain exemplary embodiments according to the present disclosure, certain examples of which are illustrated in the accompanying drawings.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. To the extent publications and patents or patent applications incorporated by reference contradict the invention contained in the specification, the specification will supersede any contradictory material.

In this application, the use of the singular includes the plural unless specifically stated otherwise. Also in this application, the use of "or" means "and/or" unless stated otherwise. Furthermore, the use of the term "including," as well as other forms, such as "includes" and "included," are not limiting. Any range described herein will be understood to include the endpoints and any values between the endpoints.

Disclosed herein are methods for preparing tissue products having reduced immunogenicity when implanted in humans or non-human primates by removing some or all alpha-gal epitopes. Various human or other animal tissues and various methods can be used to prepare the tissue products. For example, the compositions can be prepared by selecting a porcine tissue; optionally decellularizing the tissue to produce a collagen-containing tissue matrix; and exposing the tissue to one or more proteases, e.g., alcalase, bromelain, trypsin, and/or dispase, for a period of time and at a concentration sufficient to remove a desired amount of alpha-gal moieties. In some embodiments, the removal of alpha-gal moieties can be measured and/or confirmed following exposure to the protease. In certain embodiments, the enzyme can include an enzyme that is not an alpha-galactosidase, i.e., is not specific for alpha-galactose cleavage.

In various embodiments, the tissue products can comprise intact tissue, partially or completely decellularized tissue matrices, and/or decellularized tissues that have been seeded with one or more cells. In some embodiments, removal of some or all of the alpha-gal epitopes can be confirmed, e.g., by direct measurement and comparison of the alpha-gal concentration on the surface of a sample of the protease-treated tissue product against the concentration in an untreated tissue. In some embodiments, removal can be confirmed by comparison of the immune and/or inflammatory response in the protease treated tissue against the response in an untreated tissue.

As used herein, the term "tissue matrix" refers to a three-dimensional collagen and protein structure forming a network of fibers having a shape and orientation similar to the shape and orientation of a the collagen and protein network found in a naturally occurring tissue. Cells from the naturally occurring tissue can be removed to provide an acellular tissue matrix.

According to various embodiments, the materials and methods provided herein can be used to make a tissue product that is a biocompatible implant (e.g., a biocompatible tissue graft). As used herein, a "biocompatible" implant is one that has the ability to support the migration and proliferation of native cells from surrounding tissue into an implanted tissue product and/or to be implanted without inducing a substantial immune response. As used herein, the terms "native cells" and "native tissue" mean the cells or tissue present in the recipient organ or tissue prior to implantation of a tissue product, or the cells or tissue produced by the host animal after implantation. Biocompatible implants may support native cellular activity necessary for tissue regeneration, repair, healing, or treatment and may not elicit a substantial immune response that prevents such cellular activity. As used herein, a "substantial immune response" is one that prevents partial or complete tissue regeneration, repair, healing, or treatment.

The tissue products produced according to the methods discussed herein can be used, in certain embodiments, to regenerate, repair, replace, heal, augment, reinforce, and/or treat native tissues that have been damaged or lost due to various diseases and/or structural damage (e.g., from trauma, surgery, atrophy, and/or long-term wear and degeneration). The compositions of the present disclosure can also be used, in certain embodiments, for cosmetic purposes to repair or alter the appearance or feel of a native tissue. The tissue products made using the methods discussed herein can have reduced inflammatory responses or other responses and therefore may reduce the possibility of implant rejection (e.g., due to an immune response to xenogenic epitopes such as alpha-gal on a tissue product). For example, a tissue product substantially free of alpha-gal moieties can be used as a tissue graft, thereby reducing the risk of rejection or an inflammatory immune response to the graft.

Removal of Alpha-1,3-Galactose Epitopes

In various embodiments, alpha-gal epitopes can be removed from a tissue product prior to transplantation by exposing the tissue product to a protease such as alcalase, bromelain, trypsin, or dispase at a sufficient concentration and for a period of time sufficient to remove a desired amount of alpha-gal epitopes. In some embodiments, the protease enzyme is selected for its ability to remove alpha-gal while minimizing damage to the extracellular matrix of the tissue. In some embodiments, the methods herein are used to remove alpha-gal without damaging the extracellular matrix of the tissue.

In various embodiments, the enzymes, enzyme concentrations, and treatment times are also selected to control other mechanical or biological properties. For example, the enzymes and treatment conditions may be selected to produce a tissue product with desirable mechanical or biological properties as described in copending U.S. application Ser. No. 13/457,791 and Ser. No. 14/019,274.

In various embodiments, the methods disclosed herein can be used to remove a sufficient amount of alpha-gal moieties such that the tissue product does not induce a substantial immune response following implantation. In some embodiments, the methods disclosed herein can be used to remove substantially all the alpha-gal epitopes on a tissue product (e.g., at least about 95, 96, 97, 98, 99, 99.5, 99.9, or 99.99%, or 100%, or any percentage in between). In some embodiments, a sufficient percentage of alpha-gal epitopes are removed such that the tissue products have at least about a 10, 20, 30, 40, 50, 60, 70, 80, 90, or 100% reduction in inflammation or immune response following implantation, as compared to the response to an untreated tissue (or any percentage in between). In some embodiments, a sufficient percentage of alpha-gal epitopes are removed such that the tissue products have at least about a 2, 3, 4, 5, or more fold reduction in inflammation or immune response, as compared to the response to an untreated tissue.

The tissue products disclosed herein can comprise any tissue suitable for implantation from an animal (e.g., pigs or other non-primate mammals) following removal of alpha-gal epitopes. Tissue from one or more different animals can be used in the tissue products. The tissue can be, e.g., one or more of fascia, pericardial tissue, dura, adipose tissue, umbilical cord tissue, placental tissue, cardiac valve tissue, ligament tissue, tendon tissue, arterial tissue, venous tissue, neural connective tissue, urinary bladder tissue, ureter tissue, skin, dermal tissue, heart tissue, lung tissue, liver tissue, and intestinal tissue, among other exemplary tissue sources. In some embodiments, the tissue can be acellular, partially decellularized, and/or decellularized tissue that has been repopulated with exogenous cells, so long as the tissue retains at least some of the extracellular matrix scaffold found in native tissue prior to decellularizing. If a decellularized tissue is used, it can be decellularized before, at the same time, or after treatment to remove alpha-gal epitopes.

In some embodiments, the tissue in a tissue product is provided by harvesting from a donor tissue source. In some embodiments, the harvested tissue provides a porous extracellular scaffold structure into which cells from surrounding native tissue can migrate and proliferate after implantation of a tissue product into a host site. In some embodiments, the tissue is partially or completely decellularized. Alternatively, any other suitable decellularized tissue matrices may be used. For example, a number of biological scaffold materials are described by Badylak et al., and the methods of the present disclosure can be used to produce a tissue product using any of those materials, or any other similar materials. Badylak et al., "Extracellular Matrix as a Biological Scaffold Material: Structure and Function," *Acta Biomaterialia* (2008), doi:10.1016/j.actbio.2008.09.013, hereby incorporated by reference in its entirety.

In various embodiments, alpha-gal epitopes can be removed from a tissue in a tissue product by exposure to a protease enzyme, such as alcalase, bromelain, trypsin, or dispase at a sufficient concentration and for a period of time sufficient to remove a desired percentage of epitopes. For example, a sample of tissue can be exposed to alcalase and/or trypsin at a concentration ranging from about 0.0001% to about 0.1% (e.g., about 0.0001, 0.0002, 0.0003, 0.0004, 0.0005, 0.0006, 0.0007, 0.0008, 0.0009, 0.001, 0.005, 0.01, 0.05, or 0.1%, or any percentage in between). In some embodiments, the tissue can be exposed to the about 0.0001% to about 0.1% alcalase and/or trypsin for a period of time ranging from about 0.5 hours to about 24 hours (e.g., about 0.5, 1, 1.5, 2, 2.5, 3, 3.5, 4, 4.5, 5, 6, 7, 8, 9, 10, 15, 20, or 24 hours, or any time period in between). In some embodiments, a higher concentration of enzyme is paired with a shorter incubation time, or a lower concentration with a longer incubation time. In some embodiments, the exposure to alcalase and/or trypsin can be at a temperature ranging from about 15-40° C.

In another example, a sample of tissue can be exposed to bromelain and/or dispase at a concentration ranging from about 10 units/liter to about 200 units/liter (e.g., about 10, 15, 20, 25, 50, 75, 100, 125, 150, 175, or 200 units/liter, or any concentration in between). In some embodiments, the tissue can be exposed to about 10 units/liter to about 200 units/liter bromelain and/or dispase for a period of time ranging from about 1 hour to about 24 hours (e.g., about 1, 1.5, 2, 2.5, 3, 3.5, 4, 4.5, 5, 6, 7, 8, 9, 10, 15, 20, or 24 hours, or any time period in between). In some embodiments, a higher concentration of enzyme is paired with a shorter incubation time, and a lower concentration with a longer incubation time. In some embodiments, the exposure to bromelain and/or dispase can be at a temperature ranging from about 15-40° C.

In various embodiments, an advantage of removing alpha-gal epitopes by exposing a tissue to one or more of alcalase, bromelain, trypsin, and dispase is that these enzymes can also serve to alter the mechanical properties of the tissue, e.g., to provide a tissue exhibiting a desired level of pliability and/or softness (such as the softness and pliability of a native human tissue that is being replaced by a xenograft).

The use of these enzymes therefore may avoid or reduce the need for separate treatment steps to remove alpha-gal and to alter the mechanical properties of the tissue product, is so desired. This may reduce the processing time for the preparation of a tissue product and/or reduce the risk of tissue damage during processing and subsequent washing procedures. In some embodiments, the concentration and/or duration of exposure to one or more of alcalase, bromelain, trypsin, and/or dispase is selected to substantially remove alpha-gal epitopes and to produce a tissue product having a desired degree of pliability and/or softness.

In certain embodiments, a tissue exposed to one or more of alcalase, bromelain, trypsin, and/or dispase can be exposed to one or more additional enzymatic or chemical treatments to further remove alpha-gal epitopes or other undesirable antigens, e.g., other antigens not normally expressed by the recipient animal and thus likely to lead to an immune response and/or rejection of the implanted tissue product. For example, in certain embodiments, the tissue can be treated with alpha-galactosidase to further remove alpha-galactose ($\alpha$-gal) moieties. In other embodiments, any suitable alpha-galactosidase concentration and buffer can be used, as long as sufficient antigen removal is achieved. In addition, certain exemplary methods of processing tissues to reduce or remove alpha-1,3-galactose moieties are described in Xu et al., *Tissue Engineering, Vol.* 15, 1-13 (2009), which is hereby incorporated by reference in its entirety.

The presence or absence of alpha-gal in treated tissues can be evaluated in a number of ways. For example, in various embodiments, immunohistochemical staining or immunoassays such as ELISA assays can be used. Such staining can include, for example, binding of anti-body specific to alpha-gal to a tissue sample, and causing a reporter molecule to be formed (e.g., by binding an enzyme to the anti-body using one or more additional antibodies).

Decellularized Tissue Products

In various embodiments, a tissue product can comprise an intact or decellularized tissue from a non-primate mammal that expresses alpha-gal epitopes and from which the alpha-gal epitopes have been removed by exposing the tissue to one or more protease enzymes, such as alcalase, bromelain, trypsin, and/or dispase. In some embodiments, the tissue can be partially or completely decellularized but retains at least some components of the extracellular matrix into which native cells from tissue surrounding an implanted tissue product can migrate and proliferate, thereby enhancing the speed or overall level of repair, regeneration, healing, or treatment of native tissue. Decellularization can be done before, at the same time, and/or after exposing the tissue to one or more protease enzymes, such as alcalase, bromelain, trypsin, and/or dispase. In one embodiment, decellularization is done after exposure to the one or more proteases.

In some embodiments, a tissue product can be derived from any tissue that is suitable for decellularization and subsequent implantation. Exemplary tissues include, but are not limited to, bone, skin, adipose tissue, dermis, intestine, urinary bladder, tendon, ligament, muscle, fascia, neurologic tissue, vessel, liver, heart, lung, kidney, cartilage, and/or any other suitable tissue. In certain embodiments, the tissue product can include a decellularized soft tissue. For example, the tissue product can include partially or completely decellularized dermis. In other embodiments, the tissue product can comprise partially or completely decellularized small intestine submucosa.

Exemplary methods for decellularizing tissue are disclosed in U.S. Pat. No. 6,933,326 and U.S. Patent Application 2010/0272782, which are hereby incorporated by reference in their entirety. In various embodiments, the general steps involved in the production of a partially or completely decellularized tissue matrix include harvesting tissue from a donor source and removing cells under conditions that preserve biological and structural function. In certain embodiments, the harvested tissue can be washed to remove any residual cryoprotectants and/or other contaminants. Solutions used for washing can be any physiologically-compatible solution. Examples of suitable wash solutions include distilled water, phosphate buffered saline (PBS), or any other biocompatible saline solution.

In certain embodiments, the decellularization process includes chemical treatment to stabilize the harvested tissue so as to avoid biochemical and structural degradation before, during, or after cell removal. In various embodiments, the stabilizing solution arrests and prevents osmotic, hypoxic, autolytic, and/or proteolytic degradation; protects against microbial contamination; and/or reduces mechanical damage that can occur during decellularization of tissues that contain, for example, smooth muscle components (e.g., blood vessels). The stabilizing solution may contain an appropriate buffer, one or more antioxidants, one or more oncotic agents, one or more antibiotics, one or more protease inhibitors, and/or one or more smooth muscle relaxants.

In various embodiments, the tissue is then placed in a decellularization solution to remove some or all viable cells (e.g., epithelial cells, endothelial cells, smooth muscle cells, and fibroblasts, etc.) from the extracellular matrix without damaging the biological and/or structural integrity of the extracellular matrix. The decellularization solution may contain an appropriate buffer, salt, an antibiotic, one or more detergents (e.g., TRITON X-100™, sodium dodecyl sulfate, sodium deoxycholate, polyoxyethylene (20) sorbitan monooleate, etc.), one or more agents to prevent cross-linking, one or more protease inhibitors, and/or one or more enzymes.

In certain embodiments, decellularization completely or substantially removes all cells normally present in the tissue from which the tissue product is derived. As used herein, "substantially free of all cells" means that the tissue product contains less than 20%, 10%, 5%, 1%, 0.1%, 0.01%, 0.001%, or 0.0001% (or any percentage in between) of the cells that normally grow within the acellular matrix of the tissue prior to decellularization.

Tissue products, as disclosed herein, can comprise one or more elements comprising partially or completely decellularized tissues having an acellular tissue matrix and/or intact tissues that have not been decellularized. In one embodiment, the tissue product comprises elements having an acellular dermal tissue matrix. In certain embodiments, the decellularized tissue is selected from one or more of fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, skin, dermal tissue, heart tissue, lung tissue, liver tissue, and intestinal tissue.

In certain embodiments, after decellularization of a tissue in a tissue product, histocompatible/viable cells may optionally be seeded in the acellular tissue matrix. In some embodiments, histocompatible viable cells may be added to the matrices by standard in vitro cell co-culturing techniques prior to transplantation, or by in vivo repopulation following transplantation. In vivo repopulation can be by the migration of native cells from surrounding tissue into the tissue matrix or by infusing or injecting histocompatible cells obtained from the recipient or from another donor into the tissue matrix in situ. Various cell types can be used, including stem cells such as embryonic stem cells and/or adult stem cells. Any other viable cells that are histocompatible with the patient in which they are being implanted can also be used. In some embodiments, the histocompatible cells are mammalian cells. Such cells can promote native tissue migration, proliferation, and/or vascularization. In certain embodiments, the cells can be directly applied to the tissue matrix just before or after implantation.

In some embodiments, a tissue product can be treated to reduce a bioburden (i.e., to reduce the number of microorganisms growing on the tissue). In some embodiments, the tissue product is treated such that it lacks substantially all bioburden (i.e., the tissue product is aseptic or sterile). As used herein, "substantially all bioburden" means that the concentration of microorganisms growing on the tissue product is less than 1%, 0.1%, 0.01%, 0.001%, or 0.0001% of that growing prior to bioburden treatment, or any percentage in between. Suitable bioburden reduction methods are known to one of skill in the art and may include exposing the tissue product to radiation. Irradiation may reduce or substantially eliminate bioburden. Suitable forms of radiation can include gamma radiation, e-beam radiation, and X-ray radiation. Other irradiation methods are described in U.S. Application 2010/0272782, the disclosure of which is hereby incorporated by reference in its entirety.

In some embodiments, one or more additional agents can be added to the tissue product. In some embodiments, the additional agent can comprise an anti-inflammatory agent, an analgesic, or any other desired therapeutic or beneficial agent. In certain embodiments, the additional agent can comprise at least one added growth or signaling factor (e.g., a cell growth factor, an angiogenic factor, a differentiation factor, a cytokine, a hormone, and/or a chemokine). These additional agents can promote native tissue migration, proliferation, and/or vascularization. In some embodiments, the growth or signaling factor is encoded by a nucleic acid sequence contained within an expression vector. Preferably, the expression vector is in one or more of the viable cells that can be added, optionally, to the tissue product. As used herein, the term "expression vector" refers to any nucleic acid construct that is capable of being taken up by a cell, contains a nucleic acid sequence encoding a desired protein, and contains the other necessary nucleic acid sequences (e.g. promoters, enhancers, termination codon, etc.) to ensure at least minimal expression of the desired protein by the cell.

The tissue products, as described above, may be provided packaged, frozen, freeze-dried, and/or dehydrated. In certain embodiments, the packaged tissue products are sterile. For example, a kit can comprise a hydrated, frozen, freeze-dried, and/or dehydrated tissue product and instructions for preparing and/or using the tissue products.

Examples

The following examples serve to illustrate, and in no way limit, the present disclosure.

Enzyme Treatment of pADMs

Porcine skin was collected from an abattoir and split by physically removing the epidermis and subcutaneous fat. The remaining dermal tissue was de-contaminated using antibiotic solutions. Following de-contamination, the tissue was processed under aseptic conditions.

The dermal tissue was treated with one of the enzymes (bromelain, alcalase, or trypsin) for the specified amount of time. For both alcalase and trypsin, the concentrations used ranged from 0.1% to 0.00039% and the treatment time used ranged from 1 hour to overnight (probably 16-18 hours). The temperatures used were room temperature and 37° C. For bromelain, the concentrations used ranged from 25 units/ liter to 200 units/liter and the treatment used ranged from 6 hours to overnight (probably 16-18 hours). The temperatures used were room temperature and 37° C. For each of the three enzymes (alcalase, bromelain and trypsin), lower concentrations and/or shorter treatment times will probably also still work but those have not been tested yet. Generally, the lower the concentration, the longer the treatment time will have to be for the enzyme(s) to have an effect on the tissues. Treatment at 37° C. may also enhance the rate and/or activity of enzyme treatment such that lower concentrations and/or shorter treatment times can be used.

The tissue was then decellularized with detergents to remove viable cells. Cellular debris and residual chemicals were removed by washing in PBS. The resulting porcine acellular dermal matrix (pADM) was stored at ambient temperature until ready for use.

Alpha-Gal Detection Procedure

The presence of alpha-gal can be detected using a series of antibodies and colormetric detection reagents. Tissues are first preserved in a sucrose solution and then embedded in an embedding medium (OCT) and frozen in liquid nitrogen. The frozen blocks containing the tissues were then cut into thin (micron) sections using a cryostat microtome and placed onto a microscope slide. The slides containing the tissues were blocked with a solution to prevent non-specific binding and then incubated with a primary antibody, which is a biotinylated antibody that specifically binds to alpha-gal residues. After the first antibody was washed off, a second antibody (horseradish peroxidase conjugated streptavidin) was added to the slides. The streptavidin in the second antibody binds to the biotin in the primary antibody. After a period of incubation, the second antibody was also washed off after which a detection reagent (DAB) is added to the slides. DAB deposits a brown stain on the slide in the presence of horseradish peroxidase.

FIGS. 1A-1H are include black and white drawings representative of immunohistochemical staining for alpha-gal moieties with untreated porcine acellular dermis (no enzyme used to remove alpha-gal)(FIG. 1A), of porcine acellular dermis samples treated with bromelain (FIGS. 1E-1F), alcalase (FIGS. 1C-D), and trypsin (FIGS. 1G-H), each with and without alpha-galactosidase treatment, according to the methods of Example 1. As shown, samples treated with bromelain, trypsin, and alcalase show no staining for alpha-gal moieties.

Inhibition ELISA Quantitative Assay

Quantitative assessment of α-Gal content was measured using an inhibition ELISA assay. Various acellular dermal matrices (ADMs) were minced and incubated with anti-α-Gal antibody. After the incubation period, the supernatant containing any unbound antibody was transferred to a 96 well plate coated with α-Gal. The amount of unbound antibody present in the supernatant, which subsequently bound to the well plate, was detected using an alkaline phosphatase conjugated secondary antibody followed by p-Nitrophenyl phosphate detection substrate.

ADMs that contain high levels of α-Gal captured most if not all anti-α-Gal antibodies, leaving very little in the supernatant and thus, a low reading on the well plate. In contrast, ADMs which contain low levels of α-Gal only capture low levels, if any, of anti-α-Gal antibodies, leaving the majority of the antibodies in the supernatant. Thus, supernatants from these samples produced very high readings on the well plate.

Figure 2:
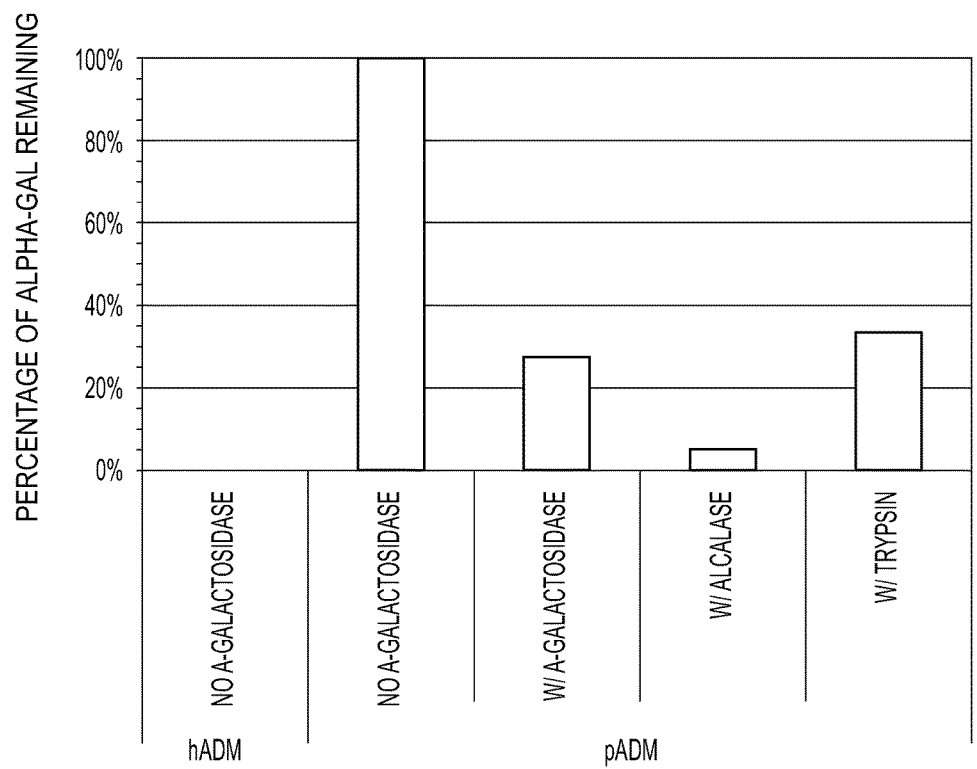
FIG. 2 illustrates results of inhibition ELISA measurements of the percentage of alpha-gal remaining in acellular dermal matrices as untreated controls, and acellular dermal matrices treated with various enzymes.

The well plate readings were normalized to both positive and negative controls. Since α-Gal is absent in human tissues but present in porcine tissues, human acellular dermal matrices (hADM) and porcine acellular dermal matrices (pADM) without α-galactosidase treatment were used as the negative control and positive controls, respectively. Treatment of pADM with α-galactosidase reduced the content of α-gal to approximately 30% of untreated pADM. Enzyme (Alcalase or Trypsin) treatment of pADMs, in the absence of α-galactosidase, reduced α-Gal content to levels comparable to, or lower than α-galactosidase treatment (FIG. 2).

The preceding examples are intended to illustrate and in no way limit the present disclosure. Other embodiments of the disclosed devices and methods will be apparent to those skilled in the art from consideration of the specification and practice of the devices and methods disclosed herein.

What is claimed is:

1. A method of preparing a dermal tissue product, comprising:
    selecting at least one collagen-containing tissue matrix contained within a cellular dermal tissue and containing galactose alpha-1,3-galactose moieties; and
    contacting the at least one collagen-containing tissue matrix contained within the cellular dermal tissue with alcalase under conditions sufficient to remove galactose alpha-1,3-galactose moieties from the tissue matrix contained within the cellular dermal tissue;
    thereby preparing a dermal tissue product.

2. The method of claim 1, wherein the method further comprises decellularizing the cellular dermal tissue following contacting the at least one collagen-containing tissue matrix contained within the cellular dermal tissue with alcalase.

3. The method of claim 2, wherein the tissue matrix is completely decellularized.

4. The method of claim 1, wherein galactose alpha-1,3-galactose is substantially or completely removed from the collagen-containing tissue matrix.

5. The method of claim 1, wherein the alcalase removes galactose alpha-1,3-galactose moieties without damaging the at least one tissue matrix.

6. The method of claim 1, further comprising performing an assay to determine if galactose alpha-1,3-galactose moieties have been removed from the at least one collagen-containing tissue matrix.

7. The method of claim 6, wherein the assay comprises measuring a concentration of galactose alpha-1,3-galactose moieties in the collagen-containing tissue matrix.

8. The method of claim 6, wherein the assay comprises an histochemical assay.

9. The method of claim 6, wherein the assay comprises an immunoassay.

10. The method of claim 1, wherein the alcalase is used at a concentration ranging from about 0.0001% to about 0.1% and for a period of time ranging from about 0.5 hours to about 24 hours.

11. The method of claim 1, further comprising contacting the tissue with alpha-galactosidase following contacting the at least one collagen-containing tissue matrix contained within the cellular dermal tissue with alcalase.

12. The method of claim 1, wherein tissue from one or more different animals are used.

13. The method of claim 1, wherein the at least one collagen-containing tissue matrix is a porcine tissue matrix.

14. The method of claim 2, further comprising adding one or more viable and histocompatible cells to the tissue product.

15. The method of claim 14, wherein the one or more cells are mammalian cells.

16. The method of claim 14, wherein the one or more cells are stem cells.

17. The method of claim 1, further comprising treating the at least one collagen-containing tissue matrix to reduce bioburden.

18. The method of claim 17, wherein treating the at least one collagen-containing tissue matrix to reduce bioburden comprises irradiating the tissue product.

* * * * *